US00PP37641P2

(12) United States Plant Patent
Byrne et al.

(10) Patent No.: US PP37,641 P2
(45) Date of Patent: Aug. 25, 2026

(54) PEACH TREE NAMED 'TX3C490LWP'

(50) Latin Name: *Prunus persica.*
Varietal Denomination: TX3C490LWP

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,141

(22) Filed: Sep. 22, 2025

(51) Int. Cl.
*A01H 5/08* (2018.01)
*A01H 6/74* (2018.01)

(52) U.S. Cl.
USPC ..... Plt./194

(58) Field of Classification Search
USPC ..... Plt./194
See application file for complete search history.

(56) References Cited

U.S. PATENT DOCUMENTS

PP14,627 P3 3/2004 Byrne et al.
PP14,629 P3 3/2004 Byrne et al.
PP26,119 P3 11/2015 Byrne et al.
PP27,741 P3 * 3/2017 Byrne ..... Plt./198
PP36,872 P3 * 8/2025 Byrne ..... A01H 6/7463 Plt./195

OTHER PUBLICATIONS

U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Byrne and Anderson, 2013. White Delight peach series: Four medium-chill, subacid, white-fleshed peaches. HortScience 48(8): 1056-1058.

* cited by examiner

*Primary Examiner* — Susan Mccormick Ewoldt
(74) *Attorney, Agent, or Firm* — Dentons US LLP

(57) ABSTRACT

Disclosed is a new variety of *Prunus persica* named 'TX3C490LWP'. This new variety, which requires approximately 550 chilling units of dormancy, is a peach tree of early season maturity, which produces firm, subacid, white fleshed, clingstone pantao peach fruit that has a 70-90% dark pink blush over a light yellow green ground color, and suitable for fresh market use.

5 Drawing Sheets

Latin name of the genus and species of the plant claimed: *Prunus persica.*

Variety denomination: 'TX3C490LWP'.

CROSS-REFERENCE TO RELATED APPLICATIONS

Peach trees developed under the same breeding program as 'TX3C490LWP' include the co-pending applications listed below.

| U.S. application Ser. No. | Title |
|---|---|
| U.S. 19/295,148 | PEACH TREE NAMED 'TRH2E122W' |
| U.S. 19/336,385 | PEACH TREE NAMED 'TRH2B102LW' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,370 | PEACH TREE NAMED 'TX2B449LW' |

-continued

| U.S. application Ser. No. | Title |
|---|---|
| U.S. 19/336,372 | PEACH TREE NAMED 'TX2C465CW' |
| U.S. 19/336,375 | PEACH TREE NAMED 'TRH1C104LW' |
| U.S. 19/336,377 | PEACH TREE NAMED 'TRH3C111' |
| U.S. 19/336,380 | PEACH TREE NAMED 'TRH2C108W' |
| U.S. 19/336,383 | PEACH TREE NAMED 'TRH2E116L' |
| U.S. 19/336,368 | PEACH TREE NAMED 'TRH3E88LW' |

BACKGROUND OF THE INVENTION

This invention relates to peach trees and, more specifically, to peach trees referred to as a variety of *Prunus persica* named 'TX3C490LWP', which requires approximately 550 chilling units of dormancy, produces firm, subacid, white-fleshed, clingstone pantao peach with a 70-90% dark pink blush over a light yellow green ground color that matures early in the season. The present peach tree was the result of an ongoing Stone Fruit Breeding Program in College Station, Brazos County, Texas. To this end, controlled crosses are made each year to produce seedling populations from which improved progenies are evaluated and selected.

Seeds from a cross between the medium-chill, white-fleshed, subacid peach 'White Delight One' (not patented, Byrne, D. H. and N. Anderson. 2013. 'White Delight' peach series: Four medium-chill, subacid, white-fleshed peaches. HortScience 48:1056-1058) and the medium-chill, subacid, pantao peach selection, 'TX4E311LWP' (not patented), were planted in 2014 in an experimental plot in Somerville, TX. 'TX3C490LWP' was marked for subsequent observation and noted as having exceptional characteristics in 2016. Two-year and older trees of the variety were subsequently evaluated during the 2018 through 2023 fruit growing seasons in Texas.

Regarding the parental linage of 'TX3C490LWP', 'TX4E311LWP' is a medium-chill, subacid, white-fleshed, pantao peach selected from a hybrid population of seedlings derived from crossing the low-chill, yellow-fleshed peach selection, 'TX1A123' (not patented) with the Chinese high-chill, subacid, white-fleshed, pantao peach, 'Ruipan Four' (Wang, L. 2012. Peach genetic resource in Chia. Zhengzhou Fruit Research Institute, Zhengzhou, China, not patented). 'TX1A123' was a selection from the hybrid population between two low-chill, acid-sweet, yellow-fleshed peaches, the selection 'TXW1291-1' (not patented) and the cultivar 'Thai Tiger TXW1193-1' (not patented, Byrne, D. H. and U. Boonprakob. 2008. Thai Tiger low chill peach series. HortScience 43:2226-2227). 'TXW1291-1' was selected from a large population of seedlings derived from the open pollination of the low-chill variety, 'Tropic Beauty' (not patented, Sherman, W. B. and R. E. Rouse. 1989. Five new low-chill peach cultivars. Fruit Varieties Journal 43:120).

'TX3C490LWP' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach rootstock at the nursery site in Oakdale, CA. The variety was subsequently planted and evaluated on two-year old or older trees at experimental orchards in Somerville (2018-2023), Texas. This evaluation clearly demonstrated that the re-propagated trees were true to the characteristics of the original seedling in all observable aspects.

SUMMARY OF THE INVENTION

The 'TX3C490LWP' peach is characterized as a novelty and is otherwise noteworthy by producing fruit that ripens in the early season and is firm and with a 70-90% dark pink blush over a light yellow green ground color. In this regard, the present variety of peach tree bears subacid, white-fleshed, clingstone pantao fruit that are ripe for commercial harvesting and shipment in mid-May, when the fruit is grown in the medium chill zone of Texas. 'TX3C490LWP' blooms and ripens with its female parent, 'White Delight One' (not patented, Byrne, D. H. and N. Anderson. 2013. 'White Delight' peach series: Four medium-chill, subacid, white-fleshed peaches. HortScience 48:1056-1058) and blooms a few days after and ripens approximately one month before its pollen parent, the pantao selection 'TX4E311LWP' (not patented). 'TX3C490LWP' differs from its female parent ('White Delight One') as it has a pantao fruit shape and differs from its pollen parent 'TX4E311LWP', as it has non-showy blooms and ripens approximately one month earlier. As compared to two commercial subacid, white-fleshed, pantao peaches, 'Flat Delight One' (patented, U.S. Plant Pat. No. 27,741) and 'Flat Delight Three' (patented, U.S. Plant Pat. No. 36,872), 'TX3C490LWP' has non showy rather than showy flowers, blooms with 'Flat Delight One' but blooms 7-10 days after 'Flat Delight Three' and ripens ~one week after 'Flat Delight Three' and ~4 days before 'Flat Delight One'. The new variety exhibits the potential to be commercialized in regions that have chilling requirements that are relatively low.

BRIEF DESCRIPTION OF THE DRAWINGS

This new variety of peach tree is illustrated by the accompanying photographs of three to five-year old plants grown in Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
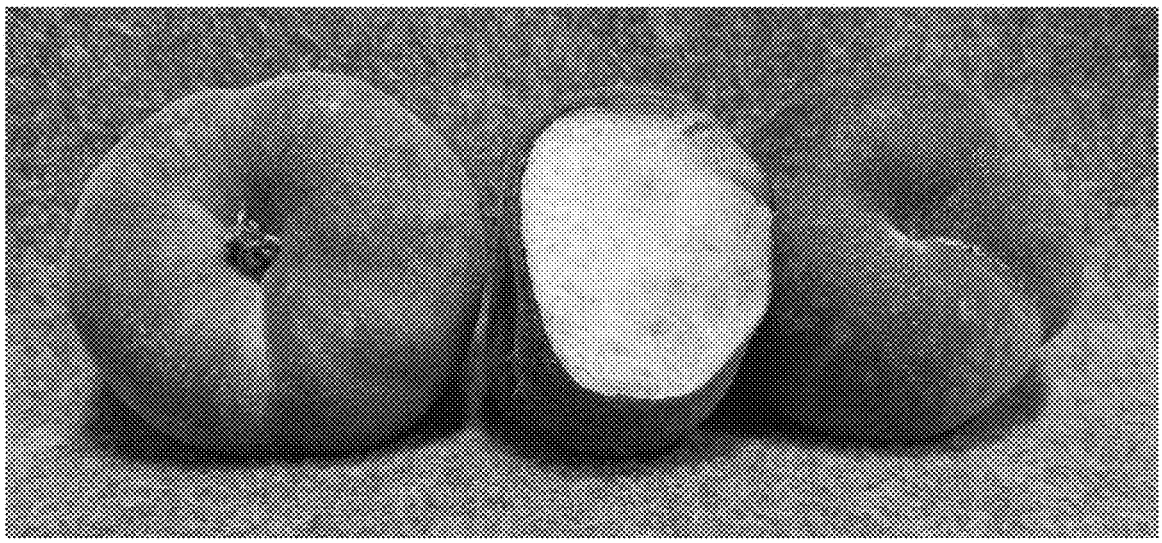
FIG. 1—Fruit of 'TX3C490LWP' produced in Fairfield, Texas showing external and internal coloration.
Figure 2:
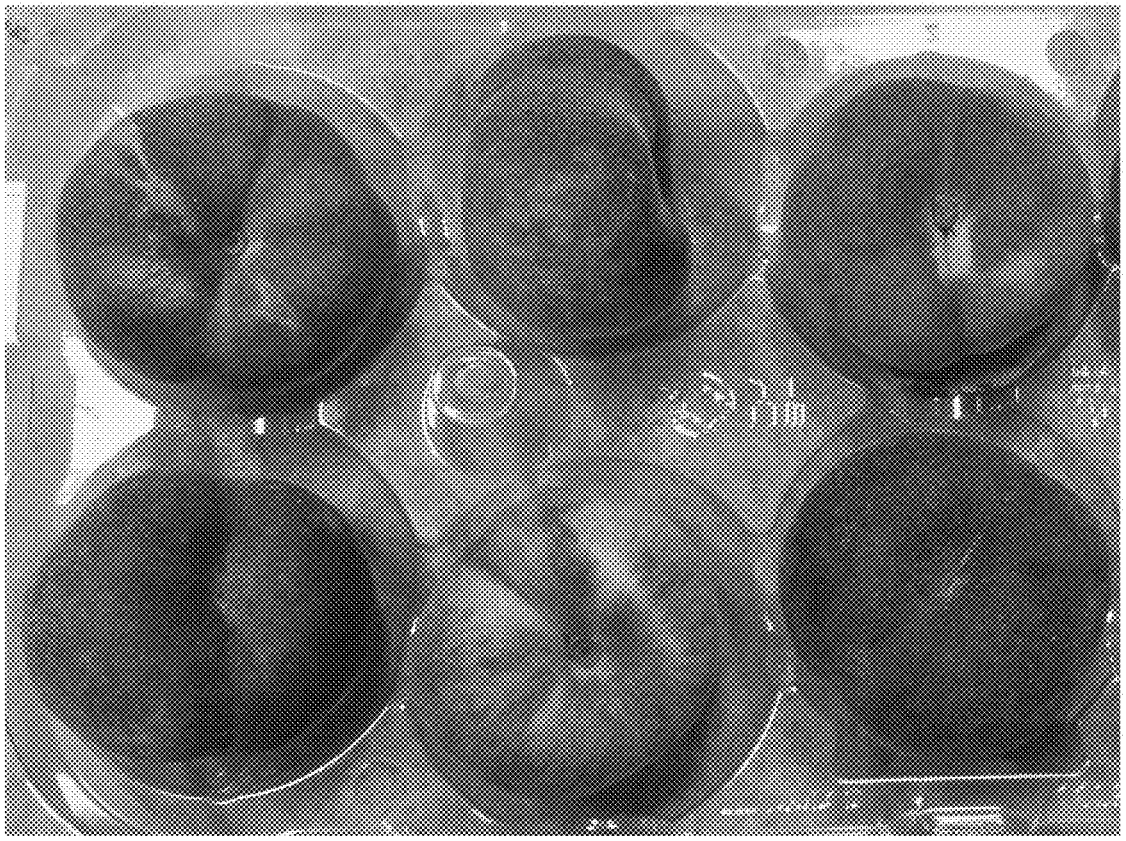
FIG. 2—'TX3C490LWP' fruit produced in Somerville, Texas.
Figure 3:
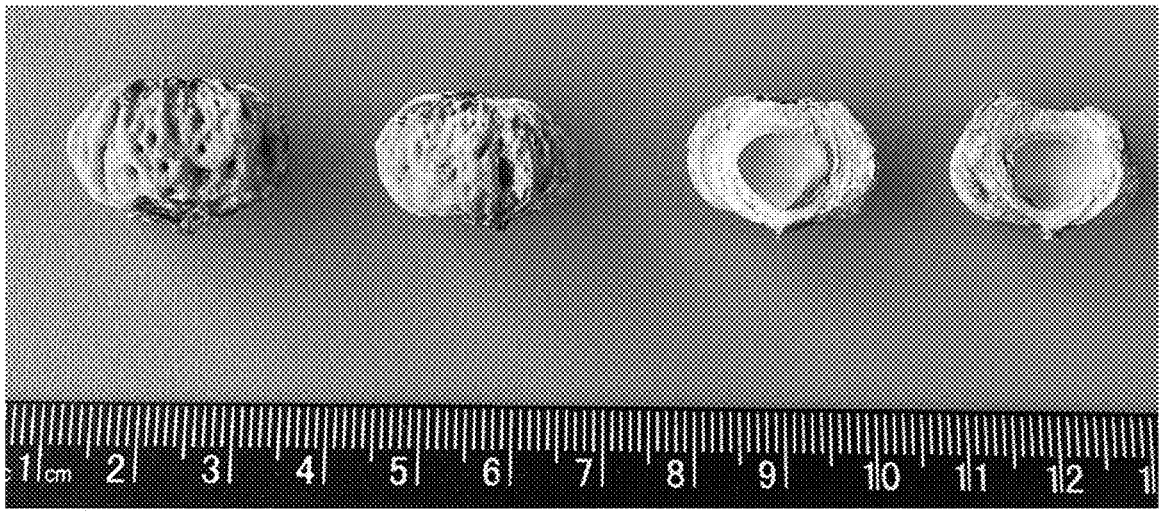
FIG. 3—Photograph of the endocarps of 'TX3C490LWP' peach. The ruler is in centimeters.
Figure 4:
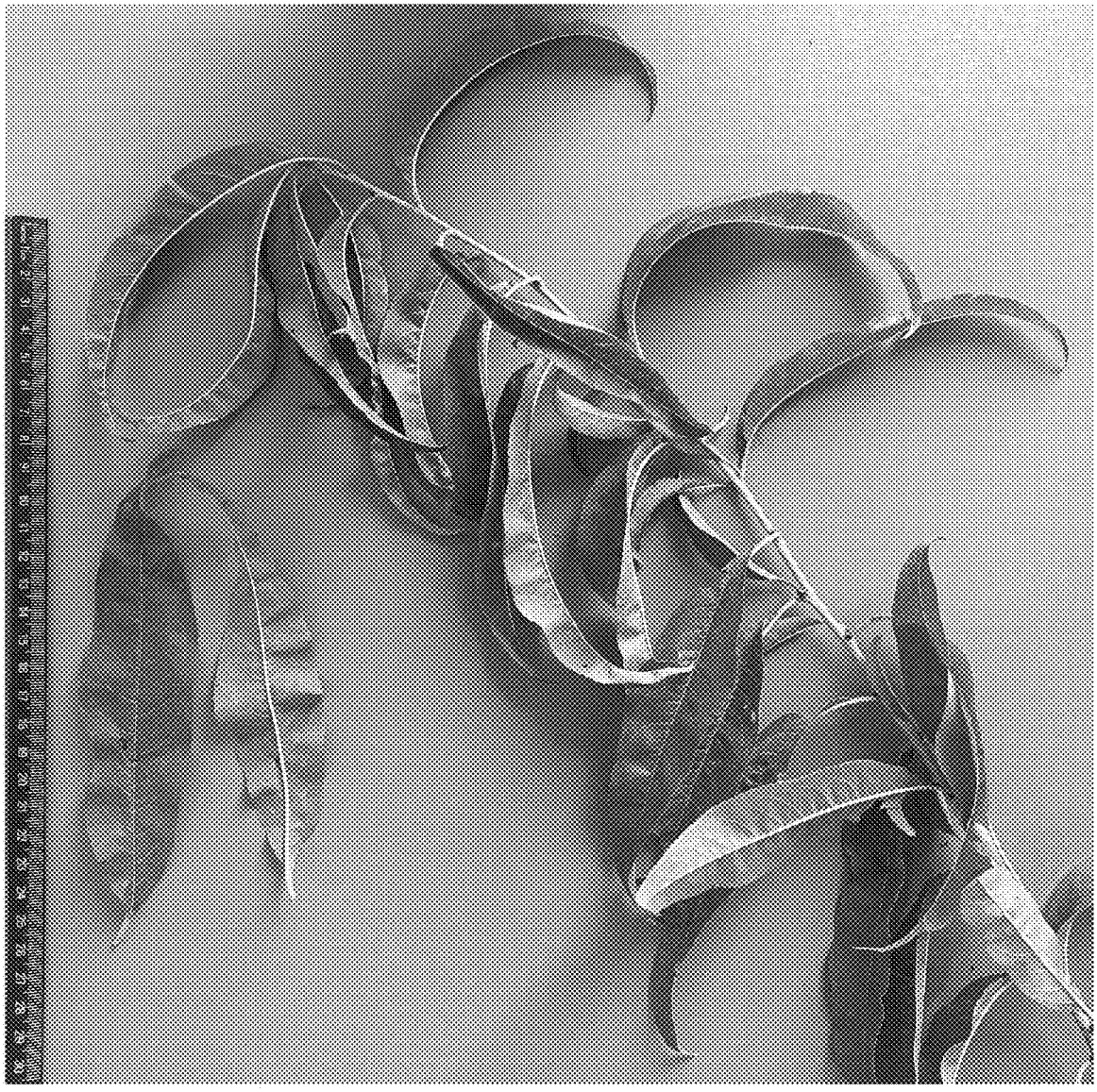
FIG. 4—A stem showing the leaves of 'TX3C490LWP' peach. The ruler is in centimeters.
Figure 5:
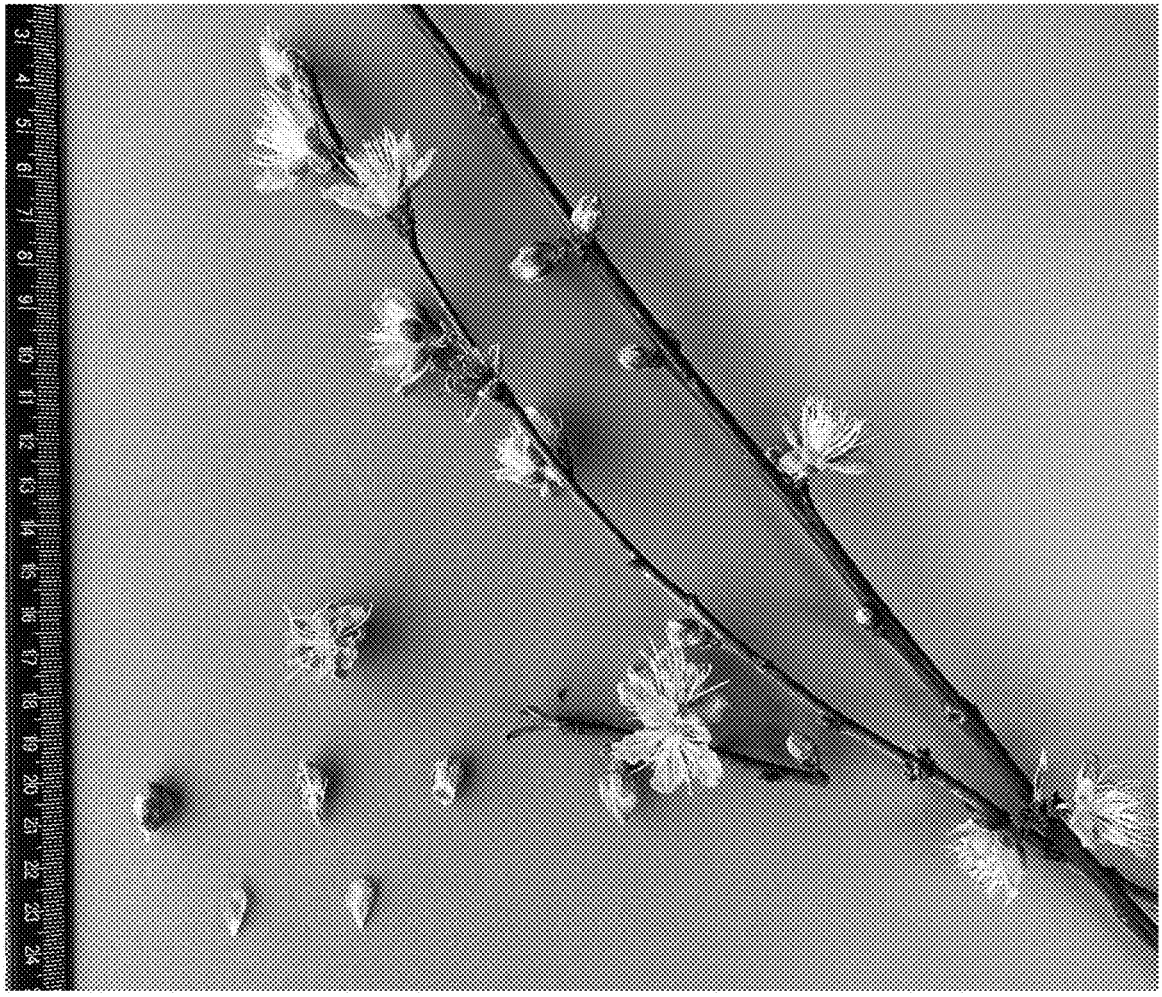
FIG. 5—A stem showing the flowers of 'TX3C490LWP' peach. The ruler is in centimeters.

Referring more specifically to the pomological details of this new and distinct variety of peach tree, the following has been observed under the ecological conditions prevailing at the experimental orchards in the medium chill zone of Texas (Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars grown in the medium chill zone of Texas.

*Height*.—9 feet (2.7 m) on a 3 year old tree at the end of the 2024 growing season.

*Width*.—9 feet width (2.7 m) on a 3 year old tree at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TX3C490LWP' peach has been trained an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 3.5 feet (0.3-1.1 m). Average vigor as compared to other commercial cultivars in the medium chill zone of Texas.

*Regularity of bearing*.—Regular in the absence of temperatures of 28° F. or below during bloom and considered hardy in the medium chill zone of Texas.

Trunk:

*Size*.—Approximately 3 inches (7.6 cm) in diameter and 9.25 inches (23.5 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS colors) present are 166A and 176A of the Greyed-Orange Group, 178A and 178B of the Greyed-Red Group, 198D of the Greyed-Green Group and N200D of the Brown Group.

Branches:

*Size*.—Considered medium for the variety.

*Thickness*.—Average (about 4 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 5 to 6 mm in width and were approximately 2 to 3 mm in height.

*Current season shoots*.—Surface texture — Substantially glabrous.

*Internode length*.—Approximately 2.2 to 3.4 cm as measured in the middle of a current season stem.

*Color of mature branches*.—The predominant colors (RHS2001) are 156D of the Greyed-White Group, 172A, 172B, 175A, 176A of the Greyed-Orange Group, 178A and 178B of the Greyed-Red Group, 198D of the Greyed-Green, N200D of the Brown Group and 201D of the Grey Group.

Leaves:

*Size*.—Considered moderately large for the species. Leaf measurements have been taken from vigorous upright current season growth approximately at mid-shoot.

*Leaf length*.—Approximately 173 to 189 mm.

*Leaf width*.—Approximately 36 to 39 mm.

*Leaf thickness*.—Approximately less than 1 mm.

*Leaf form*.—Lanceolate.

*Leaf tip form*.—Acuminate.

*Leaf upper surface color* (*RHS*2001).—Green varying among 137C and 137D of the Green Group and 146A of the Yellow-Green Group.

*Leaf lower surface color* (*RHS*2001).—Green varying among 146B and 146C of the Yellow-Green Group.

*Leaf lower mid-vein color* (*RHS*2001).—Light yellow green 145C and 145D of the Yellow-Green Group.

*Leaf margins*.—Form — Considered crenate. Uniformity — Considered generally uniform.

*Leaf petioles*.—Length — Approximately 10 to 12 mm. Thickness — Approximately 1.5 mm. Color (RHS2001) — Pale green, N144D, 145A and 146D of the Yellow-Green Group.

*Leaf glands*.—Size — Approximately 1 mm in height and less than 1 mm in width. Number — Generally 2-3 per leaf. Type — Reniform. Color (RHS2001) — Greenish brown N199B of the Grey-Brown Group and 200B and 200C of the Brown Group.

*Leaf stipules*.—Length — Approximately 8 to 10 mm. Form — Lanceolate. Color — Light green (144C, 144D, N144D and 145A of the Yellow-Green Group). The stipules are considered to be early deciduous.

*Ratio of wood* (*leaf*) *buds to flowering buds*.—Generally 2 flower buds per vegetative bud.

Flowers:

*Floral buds*.—General — The floral buds are conic in form, and slightly appressed relative to the bearing shoot. Color — The mature buds are medium to dark brown, (approximately 165A, 166A and 177A of the Greyed-Orange Group, N199B-C of the Grey-Brown Group and 200A-C and N200A of the Brown Group). Length of Mature Buds — Approximately 4 to 6 mm. Blooming type — Mean date of full bloom in the medium chill zone of Texas was in late-February (February 26$^{th}$ at Somerville), about a week after the commercial cultivar TexKing and with the commercial cultivar 'Texstar' (not patented, Byrne, D. H. and J. Kamas. 1984. 'Texstar' peach. HortScience 19(3):453-454). Flower Type — Non-showy. Flower Size — Flower diameter at full bloom is approximately 21 to 24 mm. Bloom Quantity — Considered abundant. Flower Bud Frequency — Normally 1 to 2 per node.

*Petal size*.—Width — Approximately 7 to 8 mm. Length — Approximately 11 to 13 mm.

*Petal form*.—Broadly ovate.

*Petal count*.—Nearly always 5.

*Petal abaxial/adaxial color* (*RHS*2001).—Medium to dark pink when young (62A, 62B, 62C, 63C, 63D, 65A, 65B, 68B, 68C, 70D, 73B and 73C of the Red-Purple Group), becoming darker near the petal claw.

*Petal claw*.—Form — The claw is considered truncate in shape. Length — Approximately 1 mm. Width — Approximately 1 mm.

*Petal margins*.—Generally considered variable, from nearly smooth to slightly undulate.

*Petal apex*.—Generally — The petal apices are domed.

*Flower pedicel*.—Length — Average length of 2 to 3 mm. Thickness — Approximately 1 mm. Color (RHS2001) — A light green (144D, N144D, 145B, 145C, 145D and 149D of the Yellow-Green Group).

*Floral nectaries*.—Color (RHS2001) — Light yellow (1D of the Green-Yellow Group, 2D, 3C, 3D, 4C, 4D, 5D, 6D, 8C, 8D and 9D of the Yellow Group and 16C, 16D and 18A of the Yellow-Orange Group).

*Sepals*.—Surface Texture — The surface has a short, fine, wooly texture. Size — Average Height 7.1 mm, Width 5.7 mm. Form — Ovate. Color (RHS2001) — Green with maroon (approximately 59B, 59C, 60A, 60B and 61A of the Red-Purple Group, 144D, N144D, 145A and 145B of the Yellow-Green Group, 183A, 183B, 183C, 184A, 185A, N186C, 187B and 187C of the Greyed-Purple Group).

*Floral cup* (*hypanthium*).—Surface Texture — Generally glabrous. Color (RHS2001) — Green with maroon (approximately 59B, 59C, 60A, 60B and 61A of the Red-Purple Group, 144D, N144D, 145A and 145B of the Yellow-Green Group, 183A, 183B, 183C, 184A, 185A, N186C, 187B and 187C of the Greyed-Purple Group).

*Anthers*.—General — Average in size for the species. Color (RHS2001) — Light yellow (approximately 8C, 9D, 10B, 10C, 10D, 11B, 11C, 12D and 13D of the Yellow Group and 14D, 15D, 16C, 16D, 17D, 18A, 18B, 18C and 18D of the Yellow-Orange Group). Pollen Production — Pollen is abundant and is a medium yellow color (RHS2001) (approximately 14B, 14C, 15B, 15C, 15D, 16B, 16C, 17D, 18A and 20B of the Yellow-Orange Group).

*Filaments*.—Size — Variable in length, approximately 12 to 18 mm, with the filaments slightly longer than the pistil. Color (RHS2001) — Young filaments are white (approximately 155B and 155D of the White Group) and darkening with advanced maturity.

*Pistil*.—General — Slightly shorter than the general anther height. Length — Approximately 13 to 15 mm, including the ovary. Color (RHS2001) — Considered a white to very light green when young (approximately 155A, 155B, 155C and 155D of the White Group and 157A, 157B, 157C and 157D of the Green-White Group) and becoming slightly darker with advancing senescence.

*Surface texture*.—The variety has a long, silver white pubescent pistil (approximately 155A, 155B, 155C and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in mid-May. The average ripe date at Somerville is May 10th.

*Size*.—General — Medium to medium large for the season and considered uniform.

*Average cheek diameter*.—Approximately 62 to 68 mm

*Average suture diameter*.—Approximately 68 to 74 mm

*Average axial diameter*.—Approximately 30 to 36 mm

*Fruit form*.—Generally considered flat, occasionally exhibiting unequal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Medium pink to dark red, N34A of the Orange-Red Group, 46A, 53A and 60A of the Red Group and 183A, 183B, 183C and 187C of the Greyed-Purple Group. Ventral Surface — Form — Considered uniform.

*Stem cavity*.—Width — Approximately 15 to 19 mm. Length — Approximately 17 to 24 mm. Depth — Approximately 5 to 6 mm.

*Fruit base*.—Flat.

*Fruit apex*.—Flat.

*Fruit stem*.—Length — 7 to 9 mm. Thickness — Approximately 2 mm. Color (RHS2001) — Light green, 144C, 144D, N144A, 145A, 146D and 151A of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Not observed. Skin Color — Generally-Variable, with approximately 70-90% of the fruit surface covered with an attractive dark pink blush. Blush Color (RHS2001) — Medium to very dark pink, 53A of the Red Group, 59A, 59B and 60A of the Red-Purple Group and 183A, 183B, 184A, 184B and 185A of the Greyed-Purple Group. Skin Ground Color (RHS2001) — The skin ground is a light-yellow green. Green-Yellow Group 1B, 1C and 1 D, Yellow Group 2C, 2D, 3D and Yellow-Green Group 158C and 158D. Flesh Color (RHS2001) — White, 155A, 155B, 155C and 155D of the White Group and 158C and 158D of the Yellow-White Group.

*Flesh fibers*.—Present, numerous and lightly colored. These fibers are present throughout the flesh.

*Stone cavity color*.—White, 155A, 155B, 155C, and 155D of the White Group and 158C and 158D of the Yellow-White Group.

*Flesh texture*.—Generally, the flesh is considered firm and fine at commercial maturity.

*Ripening*.—Generally the fruit of the present variety ripens evenly.

*Flavor*.—Considered very sweet (Average Brix 13.6) with a rich subacid flavor.

Stone:

*Attachment*.—Clingstone at commercial maturity.

*Stone size*.—Length — Approximately 14 to 16 mm. Width — Approximately 20 to 22 mm. Thickness — Approximately 18 to 19 mm.

*Fibers*.—Generally, there are no fibers attached along the surface of the stone.

*Stone form*.—Flat.

*Stone base*.—Very wide.

*Apex shape*.—Very wide.

*Stone shape*.—Considered flat.

*Stone surface*.—

*Surface texture*.—Consists of single pits and rosettes of pits.

*Ridges*.—Numerous fine ridges are present basally and converge towards the base of the stone.

*Ventral edge*.—Variable, from none to medium.

*Dorsal edge*.—Shape — Grooved and having moderately rough edges.

*Stone color* (*RHS*2001).—The color of the dry stone is light brown, 164B, 164C, 165C, 165D and 166D of the Greyed-Orange Group. The color of the inside surface of the endocarp is tan, 158A of the Yellow-White Group, 159A and 159B of the Orange-White Group, 161D of the Greyed-Yellow Group and 164D of the Greyed-Orange Group.

*Tendency to split*.—Splitting is relatively uncommon.

*Kernel*.—The kernel fills the endocarp at harvest and measures approximately 1-4 mm in thickness, 6-9 mm in width, and 5-7 mm in length. The colors (RHS2001) of the fresh kernels are tan with medium brown, 158A and 158B of the Yellow-White Group, 161A, 161B, 161C and 161D of the Greyed-Yellow Group and 163A, 164A, 164B, 164C and 165B of the Greyed-Orange Group. When dried the shriveled kernels measure approximately 1 mm in thickness, 6-8 mm in width and 4-8 mm in length. The colors of the shriveled kernels are tan to medium brown, 158A of the Yellow-White Group, 161A, 161B, 161C and 161D of the Greyed-Yellow Group, 163A, 164B and 164C of the Greyed-Orange Group and N199C and N199D of the Grey-Brown Group.

*Use*.—The subject variety, 'TX3C490LWP', is a peach tree which requires approximately 550 chilling units of dormancy, produces firm, subacid, white-fleshed, clingstone pantao peach with a 70-90% dark pink blush that matures early in the season and suitable for the fresh market.

*Keeping quality*.—Good. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas it will be understood that variations of the usual magnitude and characteristics incident to the changes in growing conditions, fertilization, pruning, and pest control are to be expected.

What is claimed is:

1. A new and distinct variety of peach tree named 'TX3C490LWP', as illustrated and described herein.

* * * * *